United States Patent [19]

Hsu et al.

[11] 4,236,021

[45] Nov. 25, 1980

[54] PROCESS FOR THE MANUFACTURE OF LEVULINIC ACID AND ESTERS

[75] Inventors: Chin C. Hsu, Avon Lake; Dwight W. Chasar, Northfield, both of Ohio

[73] Assignee: The B. F. Goodrich Company, Akron, Ohio

[21] Appl. No.: 36,718

[22] Filed: May 7, 1979

[51] Int. Cl.$^3$ .................. C07C 67/00; C07C 69/716; C07C 51/09; C07C 59/185
[52] U.S. Cl. ..................................... 560/174; 203/57; 203/60; 260/347.4; 562/577
[58] Field of Search ................. 560/174; 562/577; 203/57, 60

[56] References Cited

U.S. PATENT DOCUMENTS

| | | | |
|---|---|---|---|
| 2,763,665 | 9/1956 | Lock et al. | 560/174 |
| 3,203,964 | 8/1965 | Huffman et al. | 560/174 |

FOREIGN PATENT DOCUMENTS 764364  8/1971  Belgium ................................ 562/577

*Primary Examiner*—Vivian Garner
*Attorney, Agent, or Firm*—Nestor W. Shust

[57] ABSTRACT

An improved process for the manufacture of levulinic acid which comprises esterification of furfuryl alcohol in the presence of a different alcohol selected from unsubstituted primary and secondary carbon-chain or carbon-ring alcohols containing 1 to 10 carbon atoms in the presence of a small amount of acid as a catalyst, purification of the resulting levulinate ester by vacuum distillation of a mixture of the levulinate ester and a high boiling solvent and hydrolysis of the purified levulinate ester in the presence of water and a small amount of strong acid catalyst to yield levulinic acid-water mixture. The improvement resides in the purification being carried out prior to hydrolysis and in using a high boiling solvent in the purification step to prevent the formation of a solid resin.

8 Claims, No Drawings

PROCESS FOR THE MANUFACTURE OF LEVULINIC ACID AND ESTERS

BACKGROUND OF THE INVENTION

Levulinic acid esters are known to be useful as plasticizers or solvents as well as in the preparation of free levulinic acid by the hydrolysis of the ester. Levulinic acid is useful as a food-flavoring agent as well as an intermediate in the preparation of a variety of chemicals for industrial and pharmaceutical uses such as, for example, in the production of diphenolic acid, a component of protective and decorative finishes and in the preparation of calcium levulinate, a particularly suitable form of calcium for intravenous injection. The degree of actual commercial use of levulinic acid and its esters has nevertheless been rather limited because the available methods of preparation of the acid and the esters are not very practical from a commercial point of view since the yields have been rather low and the cost is relatively high.

The basic method for preparing levulinic acid esters is disclosed in U.S. Pat. No. 2,763,665 and British Pat. No. 735,693. This method comprises heating furfuryl alcohol at a temperature of 64° C. to 220° C. with a different alcohol under substantially anhydrous conditions with agitation in the presence of a catalyst such as hydrogen chloride or hydrogen bromide. It is important to maintain the concentration of furfuryl alcohol in the reaction mixture below 2% by volume of the other alcohol. The other alcohol is used in the amount of at least 4 molecular portions per molecular portion of furfuryl alcohol. U.S. Pat. No. 3,203,964 discloses an improvement of said process by incorporating in the reaction mixture a small amount of water, and also preferably premixing furfuryl alcohol with a portion of the other alcohol prior to the addition of furfuryl alcohol to the reaction mixture. It is said that in this process the other alcohol can be used in amounts as low as 2 mols of the other alcohol per mol of furfuryl alcohol. Finally, British Pat. No. 1,283,185 discloses a further modification of the basic process which comprises heating furfuryl alcohol in water with either hydrochloric or oxalic acid catalysts and in the presence of at least one mol of a water-soluble aliphatic ketone per mole of furfuryl alcohol.

SUMMARY OF THE DISCLOSURE

The instant invention is directed to an improved process for the manufacture of levulinic acid esters and the free acid. The process comprises the previously known steps of esterification of furfuryl alcohol with a different alcohol selected from the group consisting of an unsubstituted primary and secondary carbon-chain and carbon-ring alcohol in the presence of a strong acid catalyst such as hydrogen chloride, hydrogen bromide, or oxalic acid and the step of hydrolysis of the resulting ester in the presence of water and an acid catalyst. The improvement of this invention resides in the isolation of the levulinate ester by vacuum distillation of the reaction mixture containing a high-boiling solvent. The instant process yields levulinate esters in high yields without the formation of hard resinous materials which are extremely difficult to remove from the reaction vessel. Levulinic acid can be prepared, according to the prior art, by the hydrolysis of the ester. However, by using the pure distilled ester the hydrolysis time is very substantially decreased. Furthermore, the resulting levulinic acid is obtained in a pure form without the need for recrystallization.

DETAILED DISCLOSURE

The instant invention is directed to an improved process for the manufacture of levulinic acid and its esters. More specifically, it is directed to a process for the manufacture of levulinic acid esters which comprises esterification of furfuryl alcohol with a different alcohol selected from the group consisting of an unsubstituted primary and secondary carbon-chain and carbon-ring alcohol in the presence of a strong acid catalyst and hydrolysis of the ester to levulinic acid, the improvement comprising isolating the levulinate ester by vacuum distillation of the reaction mixture containing a high-boiling solvent.

As noted in the discussion of the prior art methods for the manufacture of levulinic acid, the esterification of furfuryl alcohol with a different alcohol to yield a levulinate ester as well as the hydrolysis of the ester to levulinic acid is well known in the art. The disclosures of the patents mentioned in the discussion of the background of the invention describe these steps in great detail and they are incorporated herein by reference as to the disclosure delaing with those steps. In summary, the esterification step involves the reaction of furfuryl alcohol with a different alcohol in the presence of a strong acid catalyst such as hydrogen chloride, hydrogen bromide, or oxalic acid. The next step in the prior art process is the hydrolysis of the crude ester. As a rule this step creates substantial practical problems because of the formation of a substantial amount of undesirable polymers in the reaction vessel. These polymers are very difficultly soluble in a solvent such as acetone or toluene, which would be used for cleaning the still.

As disclosed in the prior art, any alcohol as defined above may be employed in preparing levulinate esters. As illustrative examples of such alcohols may be mentioned aliphatic alcohols such as methanol, ethanol, n-propanol, isopropanol, n-butanol, isobutanol, n-pentanol, isopentanol, n-hexanol, n-octanol, n-decanol; an alkoxy-alkanol, especially alkoxyethanol such as $\beta$-methoxy ethanol, $\beta$-ethoxyethanol and the like; or a cycloaliphatic alcohol such as cyclohexanol, tetrahydrofuryl alcohol and the like. Depending on the specific alcohol employed the reaction conditions may have to be varied. For example, if a lower alkyl alcohol is used which has a relatively lower boiling point the reaction temperature may have to be lowered and consequently the reaction time lengthened. To compensate for the longer reaction time the pressure under which the reaction is carried out could be increased. Furthermore, with certain alcohols, such as lower alkanols for example, conversion to the ester is not very satisfactory and the tar formation is excessive. For these practical reasons when levulinic acid is desired as the final product n-butanol is preferably employed in the esterification step.

The critical and inventive step of the instant process is to isolate the levulinic acid ester from the reaction mixture by adding to the reaction mixture a high-boiling solvent and then distilling the reaction mixture to give pure levulinic acid ester with the byproduct polymer tar and high-boiling solvents remaining in the distillation vessel in liquid form that can easily be removed from the vessel and easily cleaned with common solvents. A further advantage of the process is that when pure levulinic acid ester is hydrolyzed to levulinic acid, the time required to substantially complete the hydrolysis is greatly reduced as compared to that when crude ester reaction mixture is hydrolyzed. Furthermore, when the acid is prepared directly from the crude ester, the acid must be recrystallized. The instant process yields pure aqueous solution of levulinic acid without recrystallization.

The amount of a high-boiling solvent needed in the distillation step depends on the amount of resin formed and the properties of the solvent and the specific ester formed. Usually the resin content is from about 2 to 10% by weight of the ester formed. Generally the ratio of the solvent to the resin should be in the range of from 1:1 to 6:1, and a more practical ratio being from 2:1 to 4:1. Expressed differently, it may be said that the high-boiling solvent should be employed in the amount of from about 3% to 20% by volume or higher of the crude ester reaction mixture. For economic reasons it is preferable to employ as little as possible of the high-boiling solvent. Generally the high boiling solvent is required in the amount of from 4% to 10% by volume.

The high-boiling solvent employed should (1) boil higher than the levulinic acid ester being distilled, (2) dissolve the tar, (3) be miscible with the levulinic acid ester being distilled, (4) be inexpensive and (5) be readily available. Clearly, the latter two enumerated properties of the high boiling solvent are preferences for practical reasons only. However, the first three enumerated properties are of critical importance because otherwise the solvent would either codistill with the ester or would not serve the purpose of maintaining tar by-products in a liquid form. It is preferable that the high boiling solvent have a boiling point of at least 20° C. above the boiling point of the levulinate being distilled, e.g., at least 50° C. above the boiling point. It is clear that the greater the boiling point differential between the levulinate ester and the solvent, the lesser the chance that even a small amount of the solvent is codistilled with the levulinate ester. Illustrative examples of high-boiling solvents are triacetin, dimethyl phthalate, diethyl phthalate, diisobutyl phthalate, di-n-butyl phthalate and the like.

Levulinic acid is obtained by the hydrolysis of the levulinate ester prepared as described above. If, according to the prior art, crude levulinate ester is hydrolyzed and then distilled to give levulinic acid, a substantial amount of tar remains in the reaction vessel which is very difficult to remove as already noted above. The hydrolysis of crude levulinate ester proceeds slowly and may require 30 to 60 hours to reach completion. By employing the improved process of this invention pure levulinate ester is employed in the hydrolysis which permits the completion of the hydrolysis step in about 3 to 6 hours, substantially improving the efficiency of the equipment. The hydrolysis step is carried out in the presence of dilute aqueous hydrochloric or hydrobromic acid, as is well known in the art. It can also be carried out both in the absence or presence of an alcohol in the initial stages of hydrolysis and, in either a nitrogen or air atmosphere. The resulting product is aqueous levulinic acid which can be concentrated by the removal of water to yield pure levulinic acid.

The following examples further illustrate the process of the instant invention without introducing any limitation thereof.

EXAMPLE 1

Preparation of Butyl Levulinate

A 50 gal. (226.8 l.) glass lined reactor equipped with an agitator, a water-cooled condenser and a cooling-/heating jacket was charged with 27.2 kg. of n-butyl alcohol. After turning on the agitator and water in the jacket for cooling, 4 lbs. (1.8 kg.) of hydrochloric acid (37%) was slowly added to the reaction vessel. The reactor was then purged with nitrogen, water was turned on in the condenser and steam turned on in the jacket to heat the reaction mixture to 96°–100° C. When the reaction mixture reached said temperature, steam was shut off and a mixture of 60 lbs. (27.2 kg.) of furfuryl alcohol and 60 lbs. (27.2 kg.) of n-butanol was added to the reactor at a rate of 1 lb. (0.45 kg.) per minute, but varying the rate of addition so as to maintain the temperature of the reaction mixture at 96°–100° C. After completion of the addition of said mixture the jacket temperature was increased to 125° C. at a rate of 2° C. per minute and the reaction mixture was allowed to reflux for one hour. Thereafter n-butanol was partially distilled off leaving behind crude butyl levulinate which had the following composition: 2.67% resin; 2.27% water; 30.54% butanol; 64.0% butyl levulinate and 0.52% others.

Following the above procedure another preparation of butyl levulinate was carried out employing 50 lb. (22.7 kg.) of furfuryl alcohol, 100 lb. (45.4 kg.) of n-butanol and 3.33 lb. (1.51 kg.) of 37% hydrochloric acid. After the removal of n-butanol, crude butyl levulinate had the following composition: 4.31% of resin; 0.49% of water; 29.19% of butanol and 65.40% of butyl levulinate.

Based on many esterification runs it was found that the resin content of the crude ester may vary from 1.5% to 10% or even 20% depending on the temperature of the reaction, the concentration of the reagents and the rate of the addition of furfuryl alcohol to the reaction mixture.

EXAMPLES 2–5

In these examples crude butyl levulinate, prepared according to the above described procedure, was employed. Distillation of the crude ester yielded the following composition: 56.5% butyl levulinate; 31.7% n-butanol; and 11.8% resin. At the end of the distillation the material remaining in the flask massively precipitated. After cooling the material became hard and could not be removed except by mechanical means, and even then with great difficulty.

350 ml. (317.8 g.) of crude butyl levulinate and 35 ml. of a high boiling solvent (10% by volume of crude levulinate) as indicated in Table I below were distilled through a 30 cm. Vigeroux column yielding first n-butanol and thereafter pure butyl levulinate in the amount indicated in the Table.

TABLE I

| Ex. No. | Solvent | b.p. °C. | Head Temp. | Pres. mm. | % Bu Levulinate Recovered |
|---|---|---|---|---|---|
| 2 | Triacetin | 258–60° | 82.5–88.5° C. | 1.45–1.9 | 57.7% |
| 3 | Dimethyl Phthalate | 282–85° | 82–92° C. | 1.65–1.8 | 58.0% |
| 4 | Di-n-butyl | | | | |

TABLE I-continued

| Ex. No. | Solvent | b.p. °C. | Head Temp. | Pres. mm. | % Bu Levulinate ♀ Recovered |
|---|---|---|---|---|---|
| 5 | Phthalate Diethyl | 340° | 85–90° C. | 1.7–1.85 | 59.5% |
|   | Phthalate | 296° | 89–95° C. | 2.0–2.2 | 57.8% |

♀ Based on the total crude butyl levulinate

The resinous material remaining in the distillation vessel was flowable and was readily dissolved in acetone.

EXAMPLE 6

The procedure of Example 2 was repeated, except that only 18 ml. of di-n-butyl phthalate (5% by volume of crude levulinate) was employed, 185.59 g. of pure butyl levulinate (84°–89° C., 1.55–1.80 mm.) was obtained.

The resinous tar remaining in the distillation flask was easily removed and was soluble in acetone.

EXAMPLE 7

The procedure of Example 2 was repeated, except that only 14.0 ml. of di-n-butyl phthalate (4% by volume of crude levulinate) was employed. 189.08 g. of pure butyl levulinate (83°–88° C., 1.5–1.8 mm.) was obtained.

The resinous tar remaining in the distillation vessel was flowable and was soluble in acetone.

EXAMPLE 8

The procedure of Example 2 was repeated, except that only 10.5 ml. of di-n-butyl phthalate (3% by volume of crude levulinate) was employed. 190.22 g. of pure butyl levulinate (82.5°–88° C., 1.4–1.7 mm.) was obtained.

The resinous tar remaining in the distillation vessel was thick and not easily removed and was not readily soluble in acetone.

EXAMPLE 9

Preparation of Levulinic Acid

Pure butyl levulinate (100 g.) obtained after distillation as described in the above examples and 150 g. of distilled water were charged into a vessel equipped with a condenser. To this mixture was added concentrated hydrochloric acid (7.5 g.). The mixture was heated to the reflux temperature and maintained at that temperature for 4 hours. During refluxing butanol was removed while water was returned to the reaction mixture. The remaining material is an aqueous solution of pure levulinic acid. Water can be distilled off to the extent desired. The aqueous acid solution had Gardner color index 2.5 which is pale straw yellow indicating high purity of the acid.

We claim:

1. In the process for the manufacture of a levulinic acid ester which comprises the esterification of furfuryl alcohol with a different alcohol selected from the group consisting of unsubstituted primary and secondary carbon-chain aliphatic and carbon-ring cycloaliphatic alcohols of 1–10 carbon atoms in the presence of a strong acid catalyst, the improvement comprising purification of the crude levulinate ester by vacuum distillation of said levulinate in admixture with at least 3 percent by volume of the levulinate of a solvent which (a) has the boiling point of at least 20° C. higher than the boiling point of the levulinate ester, (b) dissolves the by-product polymer tar and (c) is miscible with the levulinate ester.

2. A process of claim 1 wherein the difference between the boiling point of the levulinate ester and the boiling point of the solvent is at least 50° C.

3. A process of claim 1 wherein said solvent is selected from the group consisting of triacetin, dimethyl phthalate, di-n-butyl phthalate and diethyl phthalate.

4. A process of claim 3 wherein furfuryl alcohol is esterified with an aliphatic alcohol.

5. A process of claim 3 wherein the solvent is used in the amount of from 4 to 10% by volume of the crude levulinate ester.

6. A process of claim 5 wherein the distilled levulinate ester is hydrolyzed to yield pure levulinic acid.

7. A process of claim 1 wherein furfuryl alcohol is esterified with n-butanol and the solvent is di-n-butyl phthalate.

8. A process of claim 1 wherein the distilled levulinate ester is hydrolyzed to yield pure levulinic acid.

* * * * *